(12) United States Patent
Laude

(10) Patent No.: US 8,876,375 B2
(45) Date of Patent: Nov. 4, 2014

(54) COLOR CODED DENTAL X-RAY POSITIONING DEVICE

(75) Inventor: Rene G. Laude, Elgin, IL (US)

(73) Assignee: DENTSPLY International Inc., York, PA (US)

( * ) Notice: Subject to any disclaimer, the term of this patent is extended or adjusted under 35 U.S.C. 154(b) by 38 days.

(21) Appl. No.: 12/072,064

(22) Filed: Feb. 21, 2008

(65) Prior Publication Data
US 2014/0079190 A1 Mar. 20, 2014

Related U.S. Application Data

(60) Provisional application No. 60/902,786, filed on Feb. 22, 2007.

(51) Int. Cl.
| | |
|---|---|
| *A61B 6/14* | (2006.01) |
| *A61B 6/00* | (2006.01) |
| *G03B 42/02* | (2006.01) |
| *G03B 42/04* | (2006.01) |

(52) U.S. Cl.
CPC .............. *A61B 6/14* (2013.01); *A61B 6/4283* (2013.01); *A61B 6/589* (2013.01); *G03B 42/025* (2013.01); *G03B 42/042* (2013.01); *A61B 6/145* (2013.01)
USPC ........................................... 378/170

(58) Field of Classification Search
USPC .............................. 378/38, 167, 168, 170, 191
See application file for complete search history.

(56) References Cited

U.S. PATENT DOCUMENTS

| | | | |
|---|---|---|---|
| 4,866,750 A | 9/1989 | Chavarria et al. | |
| 5,044,009 A | 8/1991 | Klauser | |
| 6,033,111 A | 3/2000 | Winters et al. | |
| 6,190,042 B1 * | 2/2001 | Dove et al. | 378/170 |
| 6,343,875 B1 * | 2/2002 | Eppinger et al. | 378/170 |
| 6,944,262 B2 | 9/2005 | Massie | |
| 7,036,985 B2 * | 5/2006 | Puente et al. | 378/170 |
| 7,070,326 B2 | 7/2006 | Manley | |
| 7,290,928 B2 * | 11/2007 | Calderwood et al. | 378/170 |
| 2002/0067801 A1 | 6/2002 | Gomez | |
| 2005/0047550 A1 * | 3/2005 | Yao et al. | 378/170 |
| 2005/0265522 A1 | 12/2005 | Manley | |
| 2006/0008050 A1 | 1/2006 | Massie | |

FOREIGN PATENT DOCUMENTS

| | | |
|---|---|---|
| WO | WO 02/041075 | 5/2002 |
| WO | WO 2004/066859 | 8/2004 |

* cited by examiner

*Primary Examiner* — Irakli Kiknadze
(74) *Attorney, Agent, or Firm* — Leana Levin; Douglas J. Hura; David A. Zdurne

(57) ABSTRACT

A positioning device for holding a dental x-ray imaging media during the taking of a dental x-ray includes an aiming ring, a bite block and a positioning arm extending therebetween. The bite block carries a journal or barrel for receiving a portion of the positioning arm therein such that the portion of the positioning arm thus received can rotate or move therein, such that the position between the bite block and the aiming ring can be selected in one of a plurality of positions corresponding to a position for taking one of a plurality of dental x-ray images. In another embodiment, the bite block carries a window through which a color-coded or other indicia portion of the positioning arm is positioned such that the user can view the indicia to determine the x-ray image for which the device is set.

7 Claims, 4 Drawing Sheets

COLOR CODED DENTAL X-RAY POSITIONING DEVICE

BACKGROUND OF THE INVENTION

Devices to position dental imaging media are known in the art, such as the XCP devices available from DENTSPLY International of York, Pa. Such devices often have a positioning arm affixed to bite block. The patient bits on the bite block to secure it in the oral cavity. A shelf or other means is often provided to physically engage and position an x-ray imaging media in that position. Such media includes for example, traditional x-ray film, digital sensors, phosphor plates and the like.

Often it is necessary for the dental professional to have multiple positioning devices for the taking of the different views required. In one x-ray session the professional may choose between anterior devices, posterior devices and others.

A need exists therefore for a positioning device capable of easily switching between a plurality of dental x-ray imaging positions. The device should have some indicia (such as color coding, writing, verbiage, phrases or sentences, symbols, pictures, marks, scribes, detents and the like or combinations thereof—all collectively referred to herein as color coding, indicia and the like for the sake of simplicity).

DISCLOSURE OF THE INVENTION

A positioning device for holding a dental x-ray imaging media during the taking of a dental x-ray includes an aiming ring, a bite block and a positioning arm extending therebetween. The bite block carries a journal or barrel for receiving a portion of the positioning arm therein such that the portion of the positioning arm thus received can rotate or move therein, such that the position between the bite block and the aiming ring can be selected in one of a plurality of positions corresponding to a position for taking one of a plurality of dental x-ray images. In another embodiment, the bite block carries a window through which a color-coded or other indicia portion of the positioning arm is positioned such that the user can view the indicia to determine the x-ray image for which the device is set.

BRIEF DISCLOSURE OF THE INVENTION

Figure 1:
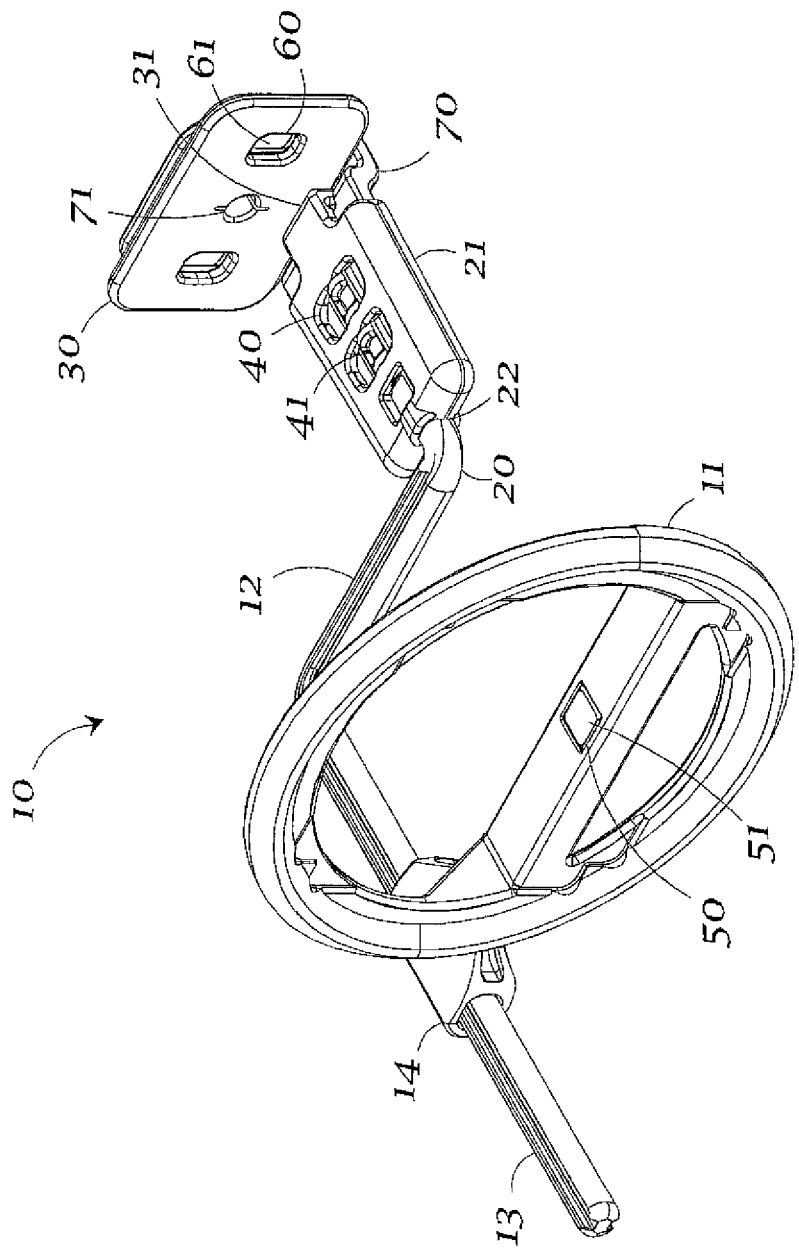
FIG. 1 is a perspective view of a positioning device embodying the concepts of the present invention, and generally set to take a posterior dental image.

A positioning device for holding a dental x-ray imaging media during the taking of a dental x-ray includes an aiming ring, a bite block and a positioning arm extending therebetween. The bite block carries a journal or barrel for receiving a portion of the positioning arm therein such that the portion of the positioning arm thus received can rotate or move therein, such that the position between the bite block and the aiming ring can be selected in one of a plurality of positions corresponding to a position for taking one of a plurality of dental x-ray images. In another embodiment, the bite block carries a window through which a color-coded or other indicia portion of the positioning arm is positioned such that the user can view the indicia to determine the x-ray image for which the device is set.

PREFERRED EMBODIMENT OF THE INVENTION

As shown on the drawings, an aiming device 10 according to the present invention includes an aiming ring 11 preferably removably affixed to a support arm 12. Support arm 12 may be configured at one end 13 to be received within a cup 14 by a friction fit. Any means of affixing ring 11 to arm 12 is within the scope of the invention. Except as may be otherwise described herein, aiming ring 11 and support arm 12 operate in a manner conventional and well-known in the dental imaging art, and which need not be further described herein.

At an end 20 of support arm 12, there is provided a means to be preferably removably affixed to a bite block 21. This means preferably includes a barrel, journal or bore 22 within which is received end 20 of support arm 12. More preferably still, end 20 is received within bore 22 in a manner such that while end 20 is held therein such as by a friction fit or the like, end 20 and hence, all of arm 12 may be freely rotated therein. Hence, arm 12 can be said to be journaled within bite block 21.

Figure 2:
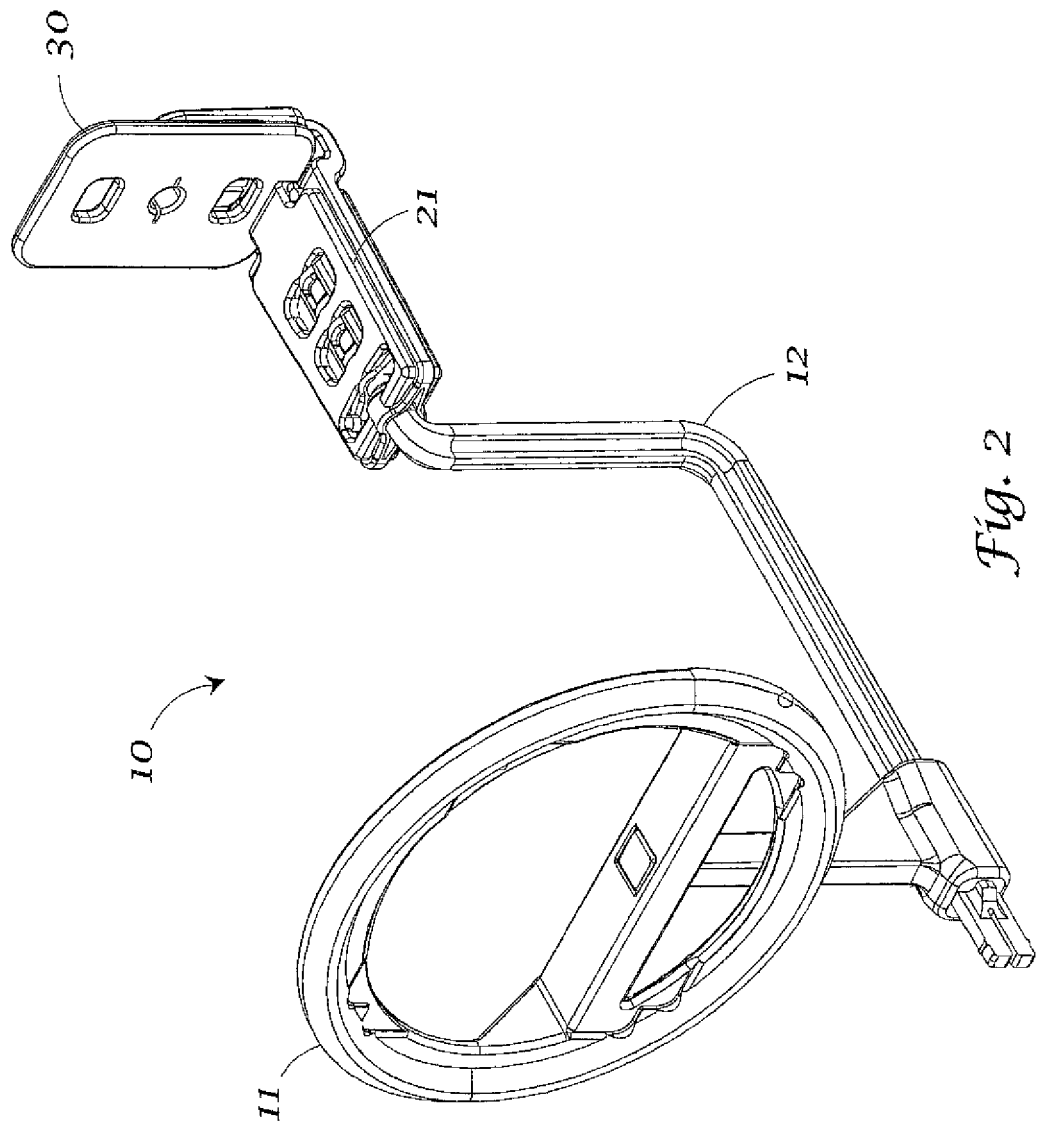
FIG. 2 is a perspective view of a positioning device as in FIG. 1 showing an alternative set to take an anterior dental image.
Figure 4:
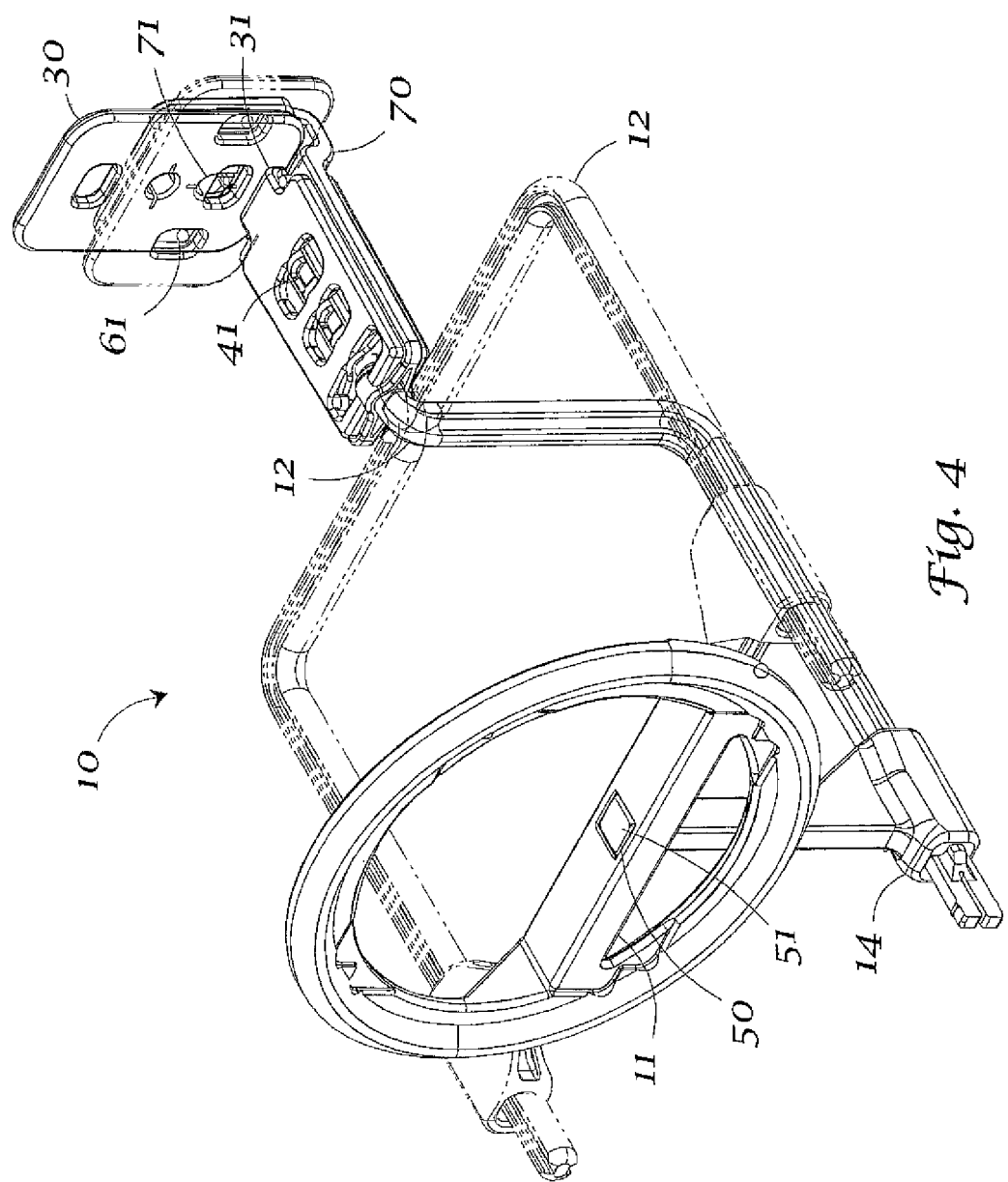
FIG. 4 is a perspective view as in FIG. 2 and showing alternative position sets in phantom lines.

A back support 30 is also provided which is used to support an image media in a conventional manner. According to the invention, back support 30 is removably affixed to bite block 21 in any conventional manner. One preferred such affixation is by using a gripping element 31 that is sized somewhat smaller than the gripped dimension of back support 30 30. By fabricating gripping element 31 from a suitable material that can be resiliently deformed, such as a plastic material, gripping element 31 can be slightly deformed to receive an edge of back support 30 and thereby hold it in that position. It will be appreciated that back plate 30 can be inserted into gripping element 31 along any of its edges, thereby allowing it to be positioned for the desired dental image. This is shown in phantom lines in FIG. 4 and as between FIGS. 1 and 2.

According to one aspect of the present invention, bite block 21 operates as any conventional bite block, but also has therein at least one window 40. End 20 of support arm 12 is provided with different color codes or other indicia 41 such that as arm 12 is rotated within bite block 21 as was above described, a different indicia 41 appears in window 40. In this manner, by properly selecting an indicia 41, the user can quickly view the indicia within window 40 and ascertain the dental image for which the device 10 is then set.

Similarly, aiming ring 11 may also be provided with a window 50 such that an indicia 51 appears therein to also signify to an observer the position within which aiming ring 11 is set. Similar again is a window 60 that may be provided in backing plate 30 having indicia 61 for similar purpose. In a preferred embodiment, a mounting arm 70 is affixed to bite block 20 and which is provided with a bearing 71 upon which is mounted backing plate 30 in a rotatable manner.

It is to be appreciated that a device 10 as described is able to provide a single alignment device that can be manually positioned between anterior and posterior positions without disassembly or the addition or removal of other parts, hardware or components. The device according to the present invention does not require tools to position the device between the anterior and posterior positions. As desired, the back support 30 or plate 30 of bite-block 20 can be re-sized to match the rectangular outline size of the image film/sensor (not shown). Such feature minimizes back support 30 from protruding beyond film/sensors' outline and provides a solid surface for a flexible image film/sensor. Via rotation, lateral translation and otherwise repositioning back support 30 components relative to one another, back support 30 outline can be changed to match the image film/sensor's outline.

By properly fabricating the appropriate components of device 10 from a suitable flexible material, such as a plastic, back support 30 outline can be changed to match image film/sensors' outline. The extent of back support 30 resizing may be limited to the number of standard film/sensor sizes it could match. Therefore, a family of product may be needed to accommodate the complete range film/sensors sizes.

Gripping element 31 of the bite-block 20 can accept and securely hold image film/sensors of different thicknesses. Securing the image film/sensor is done without harm or damage to the image film/sensor. The means of securing the image film/sensor can be accomplished by compression between a compressible, formable, malleable or otherwise flexing material and a rigid material, any combination thereof or indeed in any conventional manner without limitation.

It will be appreciated that windows 40, 50 and 60 may be translucent members, opaque members, transparent members or the like. All such variances are within the scope of the term "window" as used herein.

Figure 3:
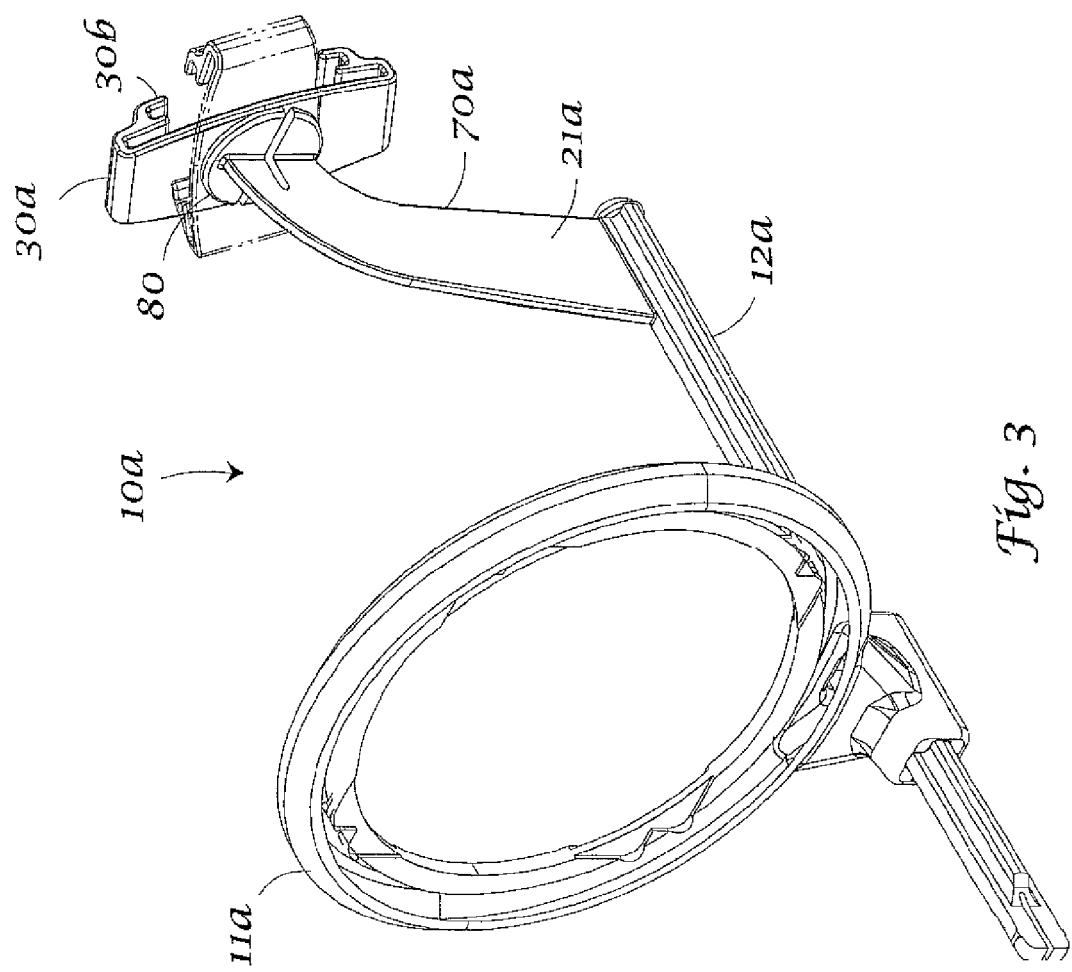
FIG. 3 is a perspective view of a positioning device as in FIG. 1 showing an alternative embodiment of the invention.

FIG. 3 shows an alternative embodiment of an aiming device 10a having an aiming ring 11a, a support arm 12a and a bite block 21a, all of which operate in a similar manner to the elements corresponding name as described hereinabove. In this embodiment, a backing plate or support 30a is provided with gripping ends 30b, configured to receive an image media (not shown) of operatively complementary configuration. Bite block 21a may also be though of as operating in a manner similar to mounting arm 70 as described above, and in such role has been tagged with the number 70a on the drawings. Backing plate 30a may be rotatably affixed to mounting arm 70a such as by spindle 80. Backing plate 30b is free to rotate to the desired position as determined by the operator.

It will be appreciated that a device 10 as described herein will carry out the objectives of the invention. The invention has been described herein with reference to the drawing figures for illustrative purposes only, without attempting to show all configurations of the invention. The scope of the invention shall be determined only by the attached claims.

What is claimed is:

1. An aiming device for the positioning of a dental image, comprising an aiming ring supported by one end of a support arm; a bite block supported by said support arm at its end generally opposite said aiming ring; said bite block having a bore therein configured to receive said support arm in a manner such that said support arm is rotatable within said bore; a window in said bite block; and an indicia carried by said support arm, such that said indicia is physically observable within said window.

2. An aiming device as in claim 1, wherein said bite block is also provided with a backing plate.

3. An aiming device as in claim 2 wherein said bite block is provided with means to removably affix said backing plate in a selected position relative said bite block.

4. An aiming device as in claim 3 wherein said means to removably affix is a deformable friction grip.

5. An aiming ring as in claim 2 wherein said backing plate is provided with a backing plate window and indicia that is physically observable within said backing plate window.

6. An aiming ring as in claim 5 wherein said backing plate is provided with at least two different indicia, one of said indicia appearing in said backing plate window at a time.

7. An aiming ring as in claim 1, wherein said aiming ring is provided with an aiming ring window and indicia that is physically observable within said aiming ring window.

* * * * *